United States Patent
Bartek

(10) Patent No.: US 12,091,370 B2
(45) Date of Patent: *Sep. 17, 2024

(54) GROWTH MEDIA FOR IMPROVED GROWTH AND YIELD OF FUNGUS USING TREATED LIGNOCELLULOSIC BIOMASS

(71) Applicant: LUSBIO, INC., San Diego, CA (US)

(72) Inventor: Robert Bartek, Centennial, CO (US)

(73) Assignee: LUSBIO, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/818,579

(22) Filed: Aug. 9, 2022

(65) Prior Publication Data

US 2022/0380271 A1 Dec. 1, 2022

Related U.S. Application Data

(63) Continuation of application No. 17/048,516, filed as application No. PCT/US2019/027452 on Apr. 15, 2019, now Pat. No. 11,427,513.

(Continued)

(51) Int. Cl.
*C05F 5/00* (2006.01)
*A01G 18/20* (2018.01)
(Continued)

(52) U.S. Cl.
CPC .............. *C05F 5/002* (2013.01); *A01G 18/20* (2018.02); *C05C 3/00* (2013.01); *C05F 11/02* (2013.01);
(Continued)

(58) Field of Classification Search
None
See application file for complete search history.

(56) References Cited

U.S. PATENT DOCUMENTS 4,333,757 A   6/1982   Kurtzman, Jr.
4,776,872 A   10/1988   Mulleavy et al.
(Continued)

FOREIGN PATENT DOCUMENTS

CN   101496485 A   8/2009
EP   1034697 A2   9/2000
(Continued)

OTHER PUBLICATIONS

International Search Report and Written Opinion for International application No. PCT/US2019/027452; dated Aug. 2, 2019 (11 pages).

(Continued)

*Primary Examiner* — Wayne A Langel
(74) *Attorney, Agent, or Firm* — Mendelsohn Dunleavy, P.C.

(57) ABSTRACT

A growth medium for fungus is obtained by: (a) treating a mixture of lignocellulosic biomass and water with at least one oxidizing agent and steam at a temperature in a range of from about 130° C. to about 220° C. for a period from about 5 seconds to about 10 hours; (b) periodically measuring a pH of the mixture for substantially an entire duration of the treating step; and (c) as necessary, based on the pH of the mixture measured in step (b), adjusting the pH of the mixture into a range of from about pH 4.5 to about pH 7.5 by adding a base to the mixture. A method for producing the growth medium for fungi and a method for cultivating fungi are also provided.

19 Claims, 1 Drawing Sheet

Related U.S. Application Data

(60) Provisional application No. 62/660,285, filed on Apr. 20, 2018.

(51) Int. Cl.
  *C05C 3/00* (2006.01)
  *C05F 11/02* (2006.01)
  *C05G 1/00* (2006.01)
  *C05G 5/40* (2020.01)
  *C12N 1/14* (2006.01)
  *C12N 1/16* (2006.01)

(52) U.S. Cl.
  CPC ............... *C05G 1/00* (2013.01); *C05G 5/40* (2020.02); *C12N 1/14* (2013.01); *C12N 1/16* (2013.01)

(56) References Cited

U.S. PATENT DOCUMENTS

| | | | |
|---|---|---|---|
| 4,848,026 | A | 7/1989 | Dunn-Coleman et al. |
| 4,990,173 | A | 2/1991 | Katz et al. |
| 5,186,731 | A | 2/1993 | Parker |
| 5,681,738 | A | 10/1997 | Beelman et al. |
| 5,934,012 | A | 8/1999 | Holtz et al. |
| 8,790,435 | B2 | 7/2014 | Parker et al. |
| 10,421,667 | B2 | 9/2019 | Foody et al. |
| 11,427,513 | B2 * | 8/2022 | Bartek ............... C12N 1/16 |
| 11,702,711 | B2 * | 7/2023 | Bartek ............... C12P 19/14 127/37 |
| 2002/0028500 | A1 | 3/2002 | Singh et al. |
| 2007/0227063 | A1 | 10/2007 | Dale et al. |
| 2014/0173977 | A1 | 6/2014 | Juscius |
| 2014/0274694 | A1 | 9/2014 | Rodriguez-Kabana et al. |
| 2016/0160239 | A1 | 6/2016 | Hoff et al. |
| 2016/0264488 | A1 | 9/2016 | Fagan et al. |
| 2018/0119090 | A1 | 5/2018 | Lipke et al. |
| 2019/0062232 | A1 | 2/2019 | Kalmbach |

FOREIGN PATENT DOCUMENTS

| | | |
|---|---|---|
| WO | WO9526626 A1 | 10/1995 |
| WO | WO03047334 A1 | 6/2003 |
| WO | WO2010129170 A2 | 11/2010 |
| WO | WO2016116113 A1 | 7/2016 |
| WO | WO2019204190 A1 | 10/2019 |

OTHER PUBLICATIONS

"Six Steps to Mushroom Farming", www.mushroomcouncil.com, 2016 [retrieved on Mar. 12, 2018] Retrieved from the Internet: <URL: https://www.mushroomcouncil.com/growing-mushrooms/six-steps-to-mushroom-farming/> (5 pages).

Extended European Search Report for corresponding European application No. 19787646.9; dated Feb. 21, 2022 (6 pages).

* cited by examiner

GROWTH MEDIA FOR IMPROVED GROWTH AND YIELD OF FUNGUS USING TREATED LIGNOCELLULOSIC BIOMASS

FIELD OF THE INVENTION

The present invention relates to growth media for fungi. In particular, the present invention is directed to fungus growth media that contain treated lignocellulosic biomass.

DESCRIPTION OF THE RELATED TECHNOLOGY

Mushrooms are traditionally farmed using compost, which provides nutrients needed for the mushrooms to grow. Compost preparation starts with thoroughly wetting a biomass such as straw, corn stover, corn cobs, shredded hardwood bark, or horse manure. Nitrogen supplements and gypsum may also be added and mixed by a turner into piles. The mixed and wetted piles are left outdoors for a composting process which employs the activity of microorganisms, heat, and some heat-releasing chemical reactions. These events result in a food source suited for the growth of mushrooms.

There must be adequate moisture, oxygen, nitrogen, and carbohydrates present during the composting process. The compost heap may be turned periodically to facilitate penetration of oxygen and moisture. Water, nitrogen supplements, or carbohydrates may be added during the composting process.

Typically, ammonia is produced during composting and thus there is a strong ammonia odor, which is usually complemented by a sweet, moldy smell. The microorganisms and chemical reactions also produce heat, which raises the temperature in the compost to over 100° F. When the compost temperatures reach 155° F. or higher, in the presence of ammonia, chemical characteristics are developed that provide a food that is used by mushrooms. This phase of the composting process may last from 7 to 14 days.

In the next phase of the composting process, the compost is pasteurized to kill pathogens, insects, nematodes, and other pests that may be present. In addition, ammonia is removed rom the compost since ammonia is lethal to mushroom spawn growth if present in a concentration higher than 0.07 wt. %. Pasteurization is achieved by raising the temperature of the compost and the surrounding air to at least 145° F. for 6 hours. The required heat may be generated by the growth of the microorganisms in the compost or by injecting steam into a pasteurization room containing the compost, or both.

After pasteurization, the compost is re-conditioned by immediately lowering the temperature to about 140° F. by flushing the pasteurization room with fresh air. Thereafter, the compost is allowed to cool gradually at a rate of approximately 2 to 3° F. each day until the ammonia dissipates. This phase of composting requires approximately 10 to 14 days to complete. The temperature of the compost is maintained at about 125° to 130° F. for optimal ammonia dissipation since de-ammonifying microorganisms grow well at these temperatures.

The compost prepared using this process is then suitable for growing mushrooms. Usually the compost has a nitrogen content of from 2.0 to 2.4 wt. %, and a moisture content between 68 and 72 wt. %. The compost may be spawned by spreading microscopic spores of mushrooms on the surface of the compost and then mixing the spores into the compost. The spores in the compost will grow into thin, thread-like cells called mycelium throughout the compost, from which mushrooms arise.

After formation of mycelium throughout the compost, a casing layer is laid atop the compost. Casing is a top-dressing applied to the spawn-run compost. Clay-loam field soil, a mixture of peat moss with ground limestone, or reclaimed weathered, spent compost can be used as the casing layer. Casing does not require nutrients since the casing acts as a water reservoir in which the mycelium fuses to form rhizomorphs that grow into full sized mushrooms.

The composting process has several drawbacks. First, the composting process is very time consuming, typically lasting from two to four weeks. Second, during the second phase of the composting process, the composted biomass is subjected to steam or air pasteurization to reduce, but not eliminate, the resident populations of microbes and pests before mushroom spawning. It is imperative that the composted biomass be treated at the required temperature to achieve uniform pasteurization, which can be difficult to achieve in the compost pile or in a poorly insulated enclosure. This may lead to incomplete pasteurization and potentially some pathogens may still be present in the compost. For example, manures of horse, cow, or poultry used in mushroom composting are known to be potential sources of pathogens like *L. monocytogenes, Salmonella* spp., pathogenic *E. coli*, and *Listeria* spp. Incomplete pasteurization can and has led to contamination of mushrooms with these pathogens. Mushroom growers are generally not required to monitor or verify that the compost is free of pathogens.

Third, the completion of the composting process is subjective, being judged, based on the observations that the compost does not smell of ammonia, has a deep brown color, has pliable stubbles, and has moisture content of from 68 wt. % to 74 wt. %. Finally, the microorganisms responsible for the composting process consume a significant portion of the carbohydrates (cellulose and hemicellulose) in the compost, in some cases, upwards of 50 wt. %, representing a significant loss of carbohydrates that could otherwise be used by the mushrooms for growth. This drawback may significantly reduce the potential yield of mushrooms per mass unit of feedstock.

To improve mushroom growth using compost, various supplements have been designed to make up the nutrients lost during the composting process. U.S. Pat. No. 5,186,731 discloses adding a supplement to either the compost or casing. The supplement includes small organic molecules that can easily be metabolized by mushrooms, such as a salt of an aliphatic, alicyclic or heterocyclic carboxylic acid. The salt is a calcium salt and/or a salt with an aliphatic, alicyclic or heterocyclic amine. In some cases, the salt is a mixture of the calcium salt of one or more aliphatic, alicyclic or heterocyclic carboxylic acids and an aliphatic, alicyclic or heterocyclic amine salt of the acid.

EP 1 034 697 A2 discloses supplementing compost with calcareous seaweed added at a concentration in the range of 1-200 kg/m$^3$, preferably 40-80 kg/m$^3$. The calcareous seaweed has a high nutrient value. Mushrooms harvested from the compost supplemented with calcareous seaweed are provided with a rich source of the trace elements, minerals and vitamins that are usually available for wild field mushrooms.

For supplementing the loss of carbohydrates during the composting process, WO 2003/047334 discloses adding a polysaccharide composition to the compost. The polysaccharide composition may include cellulose, bond paper, newsprint, straw, starch, hemicellulose, cellobiose, glycogen, or trehalose. Use of supplements adds additional cost to growing mushrooms. Further, the use of supplements does not address the long period that is required for composting.

The present invention provides a growth medium prepared from a lignocellulosic biomass, which can be produced in a short period of time by a process that can be controlled based on objective criteria. Further, a large proportion of the cellulose and hemicellulose in the lignocellulosic biomass is preserved during a treatment process that improves the bioavailability of these components for the mushrooms, such that a larger proportion of the carbohydrates from a given amount of biomass feedstock is available for mushroom growth.

SUMMARY OF THE INVENTION

In one aspect, the present invention provides a growth medium for fungus that includes biomass obtainable by:
  (a) treating a mixture of the biomass and water, with at least one oxidizing agent and steam, at a temperature in a range of from about 130° C. to about 220° C. for a period of from about 5 seconds to about 10 hours;
  (b) periodically measuring a pH of the mixture for substantially an entire duration of step (a); and
  (c) as necessary, based on the pH of the mixture measured in step (b), adjusting the pH of the mixture into a range of from about pH 4.5 to about pH 7.5 by adding a base to the mixture.

In another aspect, the present invention provides a method for producing a growth medium for fungus from a lignocellulosic biomass, including steps of:
  (a) treating a mixture of the biomass and water, with at least one oxidizing agent and steam, at a temperature in a range of from about 130° C. to about 220° C. for a period of from about 5 seconds to about 10 hours to provide treated biomass;
  (b) periodically measuring a pH of the mixture for substantially an entire duration of step (a);
  c) as necessary, based on the pH of the mixture measured in step (b), adjusting the pH of the mixture into a range of from about pH 4.5 to about pH 7.5 by adding a base to the mixture; and
  (d) adjusting a water content of the treated biomass into a range of 60-80 wt. % to provide the growth medium.

In each of the previous embodiments, the biomass may be selected from corn stover, corn cobs, palm tree empty fruit bunches, sugar cane bagasse, straw from grain crops, hay, wood waste from thinnings of deciduous and conifer forestry, sawdust from lumbering and furniture making, guayule residuals after natural rubber extraction, waste paper and cardboard.

In each of the previous embodiments, the biomass may be prewashed with demineralized water at a temperature of about 40 to 70° C. or of about 50 to 60° C. for a period of about 2 to 20 minutes or about 5 to about 10 minutes.

In each of the previous embodiments, the growth medium may further include an inert material selected from diatomaceous earth, sand, limestone chips, plastics and peat moss that may be added to the treated biomass.

In each of the previous embodiments, the growth medium may further include a nitrogen supplement selected from alfalfa press juice, monsodium glutamate, peptone, amino acids, urea, ammonium hydroxide, proteins, chicken manure, ammonium sulfate, ammonium phosphate, ammonium nitrate, calcium nitrate, brewer's grain, seed meal of soybeans, seed meal of peanuts, seed meal of cotton, and chicken manure that may be added to the treated biomass.

The nitrogen supplement may provide a nitrogen content in the growth medium in a range of from about 1.0 wt. % to about 2.0 wt. %, or from about 1.5 wt. % to about 1.7 wt. %, based on the total weight of the growth medium on a dry weight basis.

In each of the previous embodiments, the growth medium may further include a source of soluble carbon selected from carbohydrates such as glucose, galactose, mannose, fructose, maltose, xylose, arabinose, dextrin, mannitol, sucrose, starch, sorbitol, lactose and rhamnose that may be added to the treated biomass.

In each of the previous embodiments, the growth medium may further include a carbon source selected from molasses, grain, potatoes, fruits, whey, and their byproducts that may be added to the treated biomass.

In each of the previous embodiments, the growth medium may further include a proteinaceous source selected from whey, blood meal, oil seed meals, alfalfa, brewer's byproducts, and distiller's byproducts that may be added to the treated biomass.

In each of the previous embodiments, the growth medium may further include a mineral selected from salts of calcium, phosphorus, sulphur, magnesium, potassium, iron, zinc, and manganese that may be added to the treated biomass. The mineral may be a salt of calcium selected from calcium sulfate, calcium carbonate, calcium bicarbonate, and ground gypsum.

In each of the previous embodiments, the fungus may be selected from macroscopic filamentous fungi, microscopic filamentous fungi, single celled microscopic yeasts, and multicellular filamentous molds. The fungus may be selected from *Agaricus bisporus, Agaricus bitorquis, Agaricus brunnescens, Lentinus edodes, Morchella* sp., *Pleurotus* sp., *Flammulina velutipes, Volvariella volvacea, Lepisla nuda, Calocybe gambosa, Macrolepiola procera, Calvalia giganlean, Auricularia* spp., *Boletus* spp., *Letinus edodes, Canlharellus* spp., *Morchella* spp., *Pholiola nameko, Pleurotus* spp., *Slropharia rugosa-annluala, Tremeila fuciformis, Volvariella volvacea, Grifola frondosa, Ganoderma* sp., *Polporus umbellalus, Hericium erinaceus, Coprinus comalus,* and *Agrocybe* sp., *Auricularia polytricha, Enokitake, Agaricus subrufescens, Schizophyllum commune.*

In each of the previous embodiments, the at least one oxidizing agent may be selected from air, oxygen enriched air, oxygen, ozone, perchlorates, carbon dioxide, nitrous oxide, oxides, superoxides, permanganates, chlorates, peroxides, hypochlorites, or nitrates.

In each of the previous embodiments, the range for the pH of the mixture may be from about 4.5 to about 7.0, or from about 4.5 to about 6.5, or from about 4.5 to about 6.0, or from about 4.5 to about 5.5, or from about 5.5 to about 7.5, or from about 5.5 to about 7.0, or from about 6.0 to about 7.0, or from about 6.0 to about 6.5.

In each of the previous embodiments, the base may be selected from oxides, hydroxides, carbonates, borates, and halogenates of Group I and Group II elements.

In each of the previous embodiments, the base may be selected from ammonia, ammonium hydroxide, urea and combinations thereof.

In each of the previous embodiments, the temperature may be in a range of from about 130° C. to about 210° C., or from about 140° C. to about 210° C., or from about 140° C. to about 200° C., or from about 150° C. to about 200° C., or from about 150° C. to about 190° C., or from about 150° C. to about 180° C., or from about 160° C. to about 180° C., or from about 160° C. to about 170° C.

In each of the previous embodiments, the treatment process may be performed under a pressure in a range of from about 201.3 KPa to about 2068 KPa, or from about 239.2 KPa to about 1724 KPa, or from about 239.2 KPa to about 1379 KPa, or from about 308.2 KPa to about 928.7 KPa, or from about 308.2 KPa to about 790.8 KPa, or from about 308.2 KPa to about 721.9 KPa, or from about 308.2 KPa to about 652.9 KPa, or from about 308.2 KPa to about 584.0 KPa, or from about 308.2 KPa to about 515.0 KPa, or from about 308.2 KPa to about 446.1 KPa, or from about 308.2 KPa to about 377.1 KPa.

In each of the previous embodiments, the duration of the treatment process may be from about 10 seconds to about 9 hours, or from about 20 seconds to about 8 hours, or from about 30 seconds to about 8 hours, or from about 45 seconds to about 8 hours, or from about 1 minute to about 7 hours, or from about 2 minutes to about 7 hours, or from about 5 minutes to about 7 hours, or from about 10 minutes to about 6 hours, or from 15 about minutes to about 6 hours, or from about 20 minutes to about 6 hours, or from about 30 minutes to about 5 hours, or from about 5 seconds to about 1 hour, or from about 10 seconds to about 55 minutes, or from about 20 seconds to about 55 minutes, or from about 30 seconds to about 55 minutes, or from about 45 seconds to about 50 minutes, or from about 1 minute to about 50 minutes, or from 2 about minutes to about 50 minutes, or from about 5 minutes to about 50 minutes, or from about 10 minutes to about 40 minutes, or from about 15 minutes to about 40 minutes, or from about 15 minutes to about 30 minutes, or from about 1 hour to about 10 hours, or from about 1 hour to about 9 hours, or from about 1 hour to about 8 hours, or from about 1 hour to about 7 hours, or from about 1 hour to about 6 hours, or from about 1 hour to about 5 hours, or from about 1 hour to about 4 hours, or from about 1.5 hours to about 4 hours, or from about 1.5 hours to about 3 hours, or from about 1.5 hours to about 2.5 hours.

In each of the previous embodiments, the mixture may further include an oxidation catalyst selected from water insoluble metals, transition metals, precious metals, their salts or oxides, and combinations thereof.

In a further aspect, the present invention includes a method of cultivating fungus including a step of cultivating the fungus with the growth medium of any of the foregoing embodiments.

The fungus may be selected from macroscopic filamentous fungi, microscopic filamentous fungi, single celled microscopic yeasts, and multicellular filamentous molds. More specifically, the fungus may be selected from *Agaricus bisporus, Agaricus bitorquis, Agaricus brunnescens, Lentinus edodes, Morchella sp., Pleurotus sp., Flammulina velutipes, Volvariella volvacea, Lepisla nuda, Calocybe gambosa, Macrolepiola procera, Calvalia giganlean, Auricularia spp., Boletus spp., Lenlinula edodes, Canlharellus spp., Morchella spp., Pholiola nameko, Pleurolus spp., Slropharia rugosa-annluala, Tremeila fuciformis, Volvariella volvacea, Grifola frondosa, Ganoderma sp., Polporus umbellalus, Hericium erinaceus, Coprinus comalus,* and *Agrocybe sp.*

BRIEF DESCRIPTION OF THE DRAWING

FIG. 1 is a photo of corn stover that has been treated by the method of the present invention. The treated corn stover is suitable for use in a growth medium for fungi.

DETAILED DESCRIPTION OF THE PREFERRED EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It is to be understood that each component, compound, substituent or parameter disclosed herein is to be interpreted as being disclosed for use alone or in combination with one or more of each and every other component, compound, substituent or parameter disclosed herein.

It is also to be understood that each amount/value or range of amounts/values for each component, compound, substituent or parameter disclosed herein is to be interpreted as also being disclosed in combination with each amount/value or range of amounts/values disclosed for any other component(s), compounds(s), substituent(s) or parameter(s) disclosed herein and that any combination of amounts/values or ranges of amounts/values for two or more component(s), compounds(s), substituent(s) or parameters disclosed herein are thus also disclosed in combination with each other for the purposes of this description.

It is further understood that each range disclosed herein is to be interpreted as a disclosure of each specific value within the disclosed range that has the same number of significant digits. Thus, a range of from 1-4 is to be interpreted as an express disclosure of the values 1, 2, 3 and 4. It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range.

Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

The terms "biomass" and "lignocellulosic biomass" are used interchangeably and refer to plant-derived organic matter (woody or non-woody) that contains lignocellulosic polymers. Examples of biomass can include, but are not limited to, agricultural crop wastes and residues such as corn stover, wheat straw, rice straw, soybean straw, sorghum straw, barley straw, oat straw, rye straw, hay, herbs, legumes, straw of short rotation herbaceous crops such as switchgrass, alfalfa, and so forth, sugar cane bagasse, tobacco, and various weeds of any type, such as in the Bassicacae family (e.g., Arabidopsis), woody energy crops, wood wastes and residues such as trees (e.g., dogwood), including fruit-bearing trees, (e.g., apple trees, orange trees, and the like), softwood forest thinnings, barky wastes, sawdust, paper and pulp industry waste streams, wood fiber, and the like. Additional grass crops, such as various prairie grasses, including prairie cord grass, switchgrass, big bluestem, little bluestem, sideoats grama, and the like, have potential to be produced large-scale as additional plant biomass sources. For urban areas, potential plant biomass includes yard waste (e.g., grass clippings, leaves, tree clippings, brush, etc.) and vegetable processing waste.

In some embodiments, the biomass is a non-food source of waste lignocellulosic biomass, in particular leftover materials from agriculture, forestry, and the like. Specific examples include corn stover, corn cobs, empty fruit bunches of palm trees, sugar cane bagasse, straw from grain operations, wood waste from thinnings of deciduous (poplar, maple) and conifer forestry (southern yellow pine, Douglas fir), sawdust from lumbering and furniture making, guayule residuals after natural rubber extraction, and even waste paper and cardboard from municipal solid waste. In another embodiment, the biomass contains "energy grasses", which are grown for the purpose of being converted to biofuel.

The term "cellulose" as used herein refers to a natural carbohydrate, high molecular weight polymer, e.g., polysaccharide, including anhydroglucose units joined by an oxygen linkage to form long molecular chains that are essentially linear. The degree of polymerization can be about 1,000 monomer units for wood pulp to about 3,500 monomer units for cotton fiber with a molecular weight of about 160,000 g/mol to about 560,000 g/mol.

The term "fungus" as used herein refers to one of edible fungi, such as macroscopic filamentous fungi (such as mushrooms), microscopic filamentous fungi, single celled microscopic yeasts, and multicellular filamentous molds.

The term "hemicellulose" as used herein refers a polymer component of biomass that contains sugar monomers other than glucose, in contrast to cellulose, which contains only glucose. Hemicelluloses contain D-pentose sugars, and occasionally small amounts of L-sugars. In addition to glucose, hemicellulose may include xylose, mannose, galactose, rhamnose, and arabinose, with xylose being the most common sugar monomer. The sugars in hemicellulose may be linked by ester linkages as well as glycosidic linkages. Exemplary forms of hemicellulose include galactan, mannan, xylan, arabanan, arabinoxylan, glucomannan, and galactomanan.

The term "lignin" as used herein means a phenolic polymer of amorphous structure including about 17% to about 30%, by weight, of wood. Lignin is associated with cellulose and hemicellulose polymers that can make up most of the balance of the biomass. Generally, it is believed that lignin serves as a binder of cellulose and hemicellulose in biomass.

The term "lignocellulosic polymer" as used herein refers lignin, cellulose and hemicellulose polymers, where the lignin binds the cellulose and hemicellulose in a tight network (FIG. 1). Lignocellulosic polymers are a major component of the biomass. There are also lesser amounts of other compounds in the biomass, such as proteins, long chain fatty acids, salts, and minerals. In one example, the lignocellulosic polymers contain 11-25 wt. % of lignin, 8-40 wt. % of hemicellulose, and 30-57 wt. % of cellulose.

The term "treatment step" or "treating" as used herein refers to a step or process intended to alter the native biomass structure such that it can be more efficiently and economically used in a downstream process, including fermentation, agricultural uses or enzymatic conversion to chemical compounds, such as small molecule sugars, alcohols (methanol, ethanol, propanols, etc.), and small molecule hydrocarbons (methane, ethane, propane, etc.). Treatment can reduce the degree of crystallinity of lignocellulose polymers in the biomass, reduce the interference of lignin with biomass conversion and prehydrolyze some of the structural carbohydrates, thus increasing their enzymatic digestibility and/or microorganism accessibility.

The term "substantially" as used herein means an amount of at least generally about 80%, alternatively at least about 90%, alternatively at least about 95%, or alternatively at least about 99%.

In one aspect, a growth medium generated from a lignocellulosic biomass by a treatment process is provided. The treatment process includes:
 (a) treating a mixture of the biomass and water, with at least one oxidizing agent and steam, at a temperature in a range of from about 130° C. to about 220° C. for a period from about 5 seconds to about 10 hours; and
 (b) periodically measuring the pH of the mixture for substantially an entire duration of step (a), and,
 (c) as necessary, based on the pH measured in step (b) adjusting the pH of the mixture into a range of from about pH 4.5 to about pH 7.5 by adding a base to the mixture.

In a preferred embodiment, the pH of the mixture is maintained in the range of from about pH 4.5 to about pH 7.5 for substantially the entire duration of step (a).

The treatment process is designed to preferentially degrade the lignin as much as possible while preserving as much cellulose/hemicellulose for downstream use or treatment with enzymes and/or microorganisms to produce small molecule sugars, small molecule sugars, alcohols (methanol, ethanol, propanol, etc.), and small molecule hydrocarbons (methane, ethane, propane, etc.), etc., or to be used in agricultural applications as fertilizers or bases of growing compost or growing medium.

The treatment method of the present invention preferentially degrades the lignin in the biomass while preserving the cellulose and hemicellulose by controlling the pH during the treatment process to be in the range of from about 4.5 to about 7.5. Treatment in this pH range using steam and an oxidizing agent preferentially oxidizes lignin rather than the cellulose and hemicellulose in the biomass.

The treatment process uses at least one oxidizing agent to oxidize lignin, which produces carboxylic acids and $CO_2$. The produced $CO_2$ will dissolve in the treatment mixture to become carbonic acid which, together with the carboxylic acids, lower the pH of the mixture. Without pH adjustment, the pH may drop as low as 2, which provides conditions more suitable for hydrolysis of hemicellulose, and, to a lesser extent, cellulose. Further, a pH below 4.5 may also favor secondary repolymerization reactions of intermediates resulting from oxidization/hydrolysis of lignin, cellulose and hemicellulose, and other material breakdown, to thereby form larger, more bio-recalcitrant polymers that are more inert than the lignocellulosic materials.

In the present process, the pH of the treatment mixture is periodically monitored and, as necessary, adjusted to be in the range of about pH 4.5 to about pH 7.5. In some embodiments, such as when the treatment product is intended for downstream enzymatic treatment, it may be desirable to maintain the pH in the range of from about pH 4.5 to about pH 7.0, or from about pH 4.5 to about pH 6.5, or from about pH 4.5 to about pH 6.0, or from about pH 4.5 to about pH 5.5. In some other embodiments, when the treatment product is intended for downstream fermentation or agricultural applications, it may be desirable to maintain the pH in the range of from about pH 5.5 to about pH 7.5, or from about pH 5.5 to about pH 7.0, or from about pH 6.0 to about pH 7.0, or from about pH 6.0 to about pH 6.5.

The pH of the treatment mixture is monitored during the substantially the entire duration of the treatment process. As necessary, based on the measured pH value, the pH is adjusted by adding a base to the mixture. For example, the pH of the mixture may be measured continuously, or at least about 2 times, or about 5 times, or about 10 times, or about 20 times, or about 30 times, or about 40 times, or about 50 times, or about 60 times, or about 80 times, or about 100 times during the treatment process. Preferably, the pH is measured continuously or at regular time intervals, i.e. periodically.

Depending on the duration of the treatment process, pH measurements may be carried out, for example, once every second, or every about 5 seconds, or every about 10 seconds, or every about 20 seconds, or every about 30 seconds, or about 45 seconds, or every about 1 minute, or every about 2 minutes, or every about 4 minutes, or every about 6 minutes, or every about 8 minutes, or every about 10 minutes, or every about 15 minutes, or every about 20 minutes, or every about 30 minutes, or every about 1 hour.

Once the pH in the treatment mixture is measured to be lower than or approaching the lower bound of the desired pH range, a base is added to the treatment mixture to titrate acids in the mixture to adjust the pH into the desired pH range. Titration techniques well-known in the art may be employed in the treatment process. Such titration techniques may involve slowly adding the base and monitoring the pH at the same time until the pH is adjusted into the desired pH range.

Suitable bases for use in the treatment process include mineral bases, such as oxides, hydroxides, carbonates, borates and halogenates of Group I and Group II elements, i.e. alkali metals and alkaline earth metals, respectively, as well as ammonia, ammonium hydroxide, urea, or other forms of nitrogen that can form hydroxyl groups when dissolved in water. Examples of suitable metals include sodium, potassium, calcium, and magnesium compounds. Naturally occurring materials including these bases may also be used in this process. These include, but are not limited to Nahcolite, Trona, Thermonatrite, Gaylussite, Hydromagnesite, Lansfordite, Ikaite, Hydrocalcite, Dolomite, Huntite, Aragonite, Natrite, Magnesite, Calcite, Kalcinite, Gregoryite, and others. Examples of suitable bases include sodium hydroxide, potassium hydroxide, ammonium hydroxide, sodium carbonate, sodium bicarbonate and potassium carbonate, or any mixture of these. Other bases found in biological systems may also be used, including ammonia, ammonium hydroxide, urea, or other forms of nitrogen that can form hydroxyl groups when dissolved in water.

In one embodiment, the base is selected such that the base does not add to the soluble mineral burden of the treatment product, which can affect downstream treatment. Thus, the base may be selected from, for example, ammonium hydroxide and urea that are free of minerals. Further, ammonia gas may be used.

The amount of base used in the treatment process may depend on the type and age of the biomass, desired severity of the treatment, the type of base and the targeted pH during the treatment process. As an example, for a typical corn stover biomass, to control the pH of the treatment mixture to be about pH 5, the amount of sodium hydroxide required may range from about 5.5 to about 6.5 wt. % of the total weight of the corn stover under typical treatment conditions. If the pH of the treatment mixture is controlled to be about pH 4, the amount of sodium hydroxide required is about 15% less, i.e., from about 4.7 to about 5.5 wt. % of the total weight of the corn stover. If ammonium hydroxide is used to adjust the pH, the amount of base needed, by weight, will be about 12% less than when using sodium hydroxide under similar treatment conditions.

Typically, the amount of base needed for controlling the pH of the treatment mixture is in the range of from about 1 to about 10 wt. %, or from about 1 to about 9 wt. %, or from about 2 to about 9 wt. %, or from about 2 to about 8 wt. %, or from about 2 to about 7 wt. %, or from about 3 to about 7 wt. %, or from about 3 to about 6 wt. %, or from about 4 to about 6 wt. %, based on the dry weight of the biomass.

The oxidizing agent may be selected from air, oxygen enriched air, oxygen, ozone, sulfuric acid, permanganates, carbon dioxide, nitrous oxide, nitric acid, chromates, perchlorates, persulfates, superoxides, chlorates, peroxides, hypochlorites, Fenton's reagent and nitrates in which the cations may include metal cations, hydrogen ions and/or ammonium ions.

Oxidizing agents may be ranked by their strength. See Holleman et al. "Inorganic Chemistry," Academic Press, 2001, page 208. A skilled person will appreciate that, to prevent over-oxidation of the biomass, the conditions in the treatment step may be adjusted to account for the strength of the oxidizing agent. For example, when a strong oxidizing agent is used, one or more of temperature, pressure, and duration of the treatment step may be reduced to prevent over-oxidation and/or ensure that the desired degree of conversion is not exceeded. On the other hand, when a weak oxidizing agent is used, one or more of temperature, pressure, and duration of the treatment step may be increased to ensure that the desired degree of oxidation and/or conversion is achieved. When the oxidizing agent is gaseous, the pressure in the reaction vessel for the treatment step is important for ensuring the desired degree of oxidation and/or conversion. A skilled person can adjust the pressure based on common general knowledge to account for use of a gaseous oxidizing agent.

In some embodiments, oxygen is used as the oxidizing agent. In one embodiment, oxygen can be delivered in air. In some other embodiments, depending on the susceptibility of the biomass to oxidation, oxygen-enriched air can be used. Suitable enrichment can provide an oxygen concentration slightly above that of atmospheric air to an oxygen concentration of substantially pure oxygen.

Oxygen added to the treatment process may be expressed as a weight ratio of the amount of elemental oxygen to the amount of elemental carbon in the biomass (O/C on weight basis). The range of O/C can be from about 0.2 to about 1.0, or from about 0.3 to about 0.9, or from about 0.3 to about 0.8, or from about 0.4 to about 0.7, or from about 0.4 to about 0.6, or from about 0.5 to about 0.6, depending on other conditions of the treatment.

The other component introduced to the treatment process is steam. The steam may be introduced into the biomass or generated in situ from the mixture. For example, the biomass may have some moisture, or may be wetted with water before treatment. Once the temperature of the biomass is raised to above 100° C., the moisture or water in the mixture will be converted into steam. The amount of steam in the treatment mixture may range from about 0.1 to about 0.5 wt. %, or from about 0.2 to about 0.5 wt. %, or from about 0.2 to about 0.4 wt. %, based on the dry weight of the biomass. Steam may be used for one or both of controlling the pressure of the treatment step and as a heat input to the process.

The temperature of the treatment step is in the range of from about 130° C. to about 220° C., or from about 130° C. to about 210° C., or from about 140° C. to about 210° C., or from about 140° C. to about 200° C., or from about 150° C. to about 200° C., or from about 150° C. to about 190° C., or from about 150° C. to about 180° C., or from about 160° C. to about 180° C., or from about 160° C. to about 170° C.

The treatment mixture may be under an autogenous pressure or under a mild pressure during treatment. For example, the treatment mixture may be under an atmospheric pressure of 201.3 KPa. Alternatively, the pressure may be up to 2068 KPa. For example, the pressure may be in the range of from about 201.3 KPa to about 2068 KPa, or from about 239.2 KPa to about 1724 KPa, or from about 239.2 KPa to about 1379 KPa, or from about 308.2 KPa to about 928.7 KPa, or from about 308.2 KPa to about 790.8 KPa, or from about 308.2 KPa to about 721.9 KPa, or from about 308.2 KPa to about 652.9 KPa, or from about 308.2 KPa to about 584.0 KPa, or from about 308.2 KPa to about 515.0 KPa, or from about 308.2 KPa to about 446.1 KPa, or from about 308.2 KPa to about 377.1 KPa.

The treatment process can produce a treated lignocellulosic biomass suitable for fungus growth in less than a day. The treatment step may be carried out for a period of from about 5 seconds to about 10 hours, or from about 10 seconds to about 9 hours, or from about 20 seconds to about 8 hours, or from about 30 seconds to about 8 hours, or from about 45 seconds to about 8 hours, or from about 1 minute to about 7 hours, or from about 2 minutes to about 7 hours, or from about 5 minutes to about 7 hours, or from about 10 minutes to about 6 hours, or from 15 about minutes to about 6 hours, or from about 20 minutes to about 6 hours, or from about 30 minutes to about 5 hours. In some embodiments, the period for the treatment step may be in the range of from about 5 seconds to about 1 hour, or from about 10 seconds to about 55 minutes, or from about 20 seconds to about 55 minutes, or from about 30 seconds to about 55 minutes, or from about 45 seconds to about 50 minutes, or from about 1 minute to about 50 minutes, or from 2 about minutes to about 50 minutes, or from about 5 minutes to about 50 minutes, or from about 10 minutes to about 40 minutes, or from about 15 minutes to about 40 minutes, or from about 15 minutes to about 30 minutes. In some other embodiments, the period for the treating step may be in the range of from about 1 hour to about 10 hours, or from about 1 hour to about 9 hours, or from about 1 hour to about 8 hours, or from about 1 hour to about 7 hours, or from about 1 hour to about 6 hours, or from about 1 hour to about 5 hours, or from about 1 hour to about 4 hours, or from about 1.5 hours to about 4 hours, or from about 1.5 hours to about 3 hours, or from about 1.5 hours to about 2.5 hours.

It is understood that the temperature, pressure and length of the treating step are all related. For example, when the temperature is high, the length of the treating step may be reduced to prevent over-oxidation of the biomass, or when the pressure is high, the length of the treating step may also be reduced to prevent over-oxidation of the biomass. A severity factor may be used in the practice of the present invention to control the treatment process and prevent over-oxidation of the biomass.

The severity factor (SF) is defined as:

$$SF = Log\left(t * e^{\frac{T-100}{14.75}}\right)$$

where t is the duration of the treating step in minutes and T is temperature during the treating step in Celsius. It is generally considered that a higher SF value is associated with a larger proportion unwanted by-products that will reduce the yield of desirable products in downstream treatment processes.

In some embodiments, the treating step has a severity factor in the range of from about 2.5 to about 4.5, or from about 2.7 to about 4.3, or from about 2.9 to about 4.1, or from about 3.0 to about 4.0, or from about 3.2 to about 4.0, or from about 3.2 to about 3.8, or from about 3.3 to about 3.7, or from about 3.4 to about 3.6.

Mathematically, the same severity factor may be achieved by using a higher temperature in combination with a shorter treatment period or by using a longer treatment period in combination with a lower temperature. In one embodiment, a higher temperature coupled with a short treatment period may be preferred for reducing the severity factor and thereby reducing secondary polymerization reactions to favor oxidization of lignin.

In some embodiments, at least one catalyst may be added to the treatment mixture. The catalyst may catalyze the oxidation reaction by, for example, causing or enhancing formation of peroxides and superoxides, which may enhance the rate of oxygen insertion into the lignin in the biomass.

The catalyst may be selected from water insoluble metals, transition metals, and precious metals, or their salts or oxides. Examples of these metals include nickel, cobalt, platinum, palladium, rhenium, iron, copper, vanadium, zirconium and ruthenium. The catalyst may be unsupported or may be supported on inert or active matrix material such as clay, alumina, silica, silica alumina, zeolites, activated carbon, diatomaceous earth, titania, zirconia, molybdena, ceramics, and the like. Such catalysts can enhance rates of oxygen transfer, insertion and reforming of lignin in the biomass as well as being able to enhance the degree of relative oxidation. Examples of the catalysts include metal oxides, mixed metal oxides, hydroxides, and carbonates, of ceria, lanthanum, mixed rare earths, brucite, hydrotalcite, iron, clays, copper, tin, and vanadium.

In some embodiments, the catalyst is a hydrogenation catalyst including a zirconium/platinum catalyst and zirconium/palladium catalyst. Other catalyst includes noble metals such as Rh, Pd, Pt, Cu, Ru, Pt—Cu, Ni—Cu, $CoMoS_2$, $NiMoS_2$, $MoO_3$, $CrO_3$, $WO_3$, $ZrO_2$, Ni, Ag, Ge, Re, Os, and transition metals such as Li, Na, K, Mg, Ir, Ni, Cu.

The treatment process is described in co-pending application filed on Apr. 20, 2018, application No. 62/660,283, which is hereby incorporated by reference herein in its entirety.

In the present process, the pH of the treatment mixture is periodically monitored and, as necessary, adjusted to be in the range of about pH 4.5 to about pH 7.5. In some embodiments, such as when the treatment product is intended for downstream enzymatic treatment, it may be desirable to maintain the pH in the range of from about pH 4.5 to about pH 7.0, or from about pH 4.5 to about pH 6.5, or from about pH 4.5 to about pH 6.0, or from about pH 4.5 to about pH 5.5. In some other embodiments, when the treatment product is intended for downstream fermentation or agricultural applications, it may be desirable to maintain the pH in the range of from about pH 5.5 to about pH 7.5, or from about pH 5.5 to about pH 7.0, or from about pH 6.0 to about pH 7.0, or from about pH 6.0 to about pH 6.5.

The pH of the treatment mixture is monitored during the substantially the entire duration of the treatment process. As necessary, based on the measured pH value, the pH is adjusted by adding a base to the mixture. For example, the pH of the mixture may be measured continuously, or at least about 2 times, or about 5 times, or about 10 times, or about 20 times, or about 30 times, or about 40 times, or about 50 times, or about 60 times, or about 80 times, or about 100 times during the treatment process. Preferably, the pH is measured continuously or at regular time intervals, i.e. periodically.

Depending on the duration of the treatment process, pH measurements may be carried out, for example, once every second, or every about 5 seconds, or every about 10 seconds, or every about 20 seconds, or every about 30 seconds, or about 45 seconds, or every about 1 minute, or every about 2 minutes, or every about 4 minutes, or every about 6 minutes, or every about 8 minutes, or every about 10 minutes, or every about 15 minutes, or every about 20 minutes, or every about 30 minutes, or every about 1 hour.

Once the pH in the treatment mixture is measured to be lower than or approaching the lower bound of the desired pH range, a base is added to the treatment mixture to titrate acids in the mixture to adjust the pH into the desired pH range. Titration techniques well-known in the art may be employed in the treatment process. Such titration techniques may involve slowly adding the base and monitoring the pH at the same time until the pH is adjusted into the desired pH range.

During the treatment process, lignin is oxidized to small organic acids and a small amount of carbon dioxide. The lignin is also transformed from hydrophobic to hydrophilic. The partial oxidation of lignin generates heat that reduces the energy cost for heating the biomass during treatment. Further, because lignin is a thermoplastic and expands out of the pores of the biomass with heating, the porosity of the biomass is increased during the treatment process, allowing oxygen to access lignin in the interior of the biomass.

Particularly, the steam and oxygen predominantly attack lignin at onset, resulting in the formation of mostly fatty acids ranging in size from large humates, to mid-range fulvates, down to light and volatile fatty acids. The oxidative scission of lignin also results in ring opening of aromatic centers present in intermediates decoupled from lignin, removing them as potential toxic elements to fungus growth. As a result, the lignin is transformed to these smaller hydrophilic molecules which are ready food during mycelium growth phase of mushrooms. The partial oxidation and scission of lignin also reduces demand for extracellular lignases and increases the rate of further depolymerization.

The insertion of oxygen into the lignin followed by chain scission not only results in a distribution of smaller hydrophilic molecules that diffuse away from the bulk of carbohydrate fibers, but also alters the functionality of the remaining portion of lignin that is yet too large to be soluble into the surrounding water film. This change in polarity reduces its attraction to and binding of cellulose/hemicellulose fibers, increasing bundle separation by the action of water and the high concentration of mostly lignin-derived hydrophilic intermediates.

These reactions in the treatment process are significantly dissimilar from those occurring in alternative treatment processes, such as steam explosion, and dilute acid, or base catalyzed systems. These alternative processes only displace and redistribute lignin and do little to transform its hydrophobicity, structure, and inhibitory nature to fungus growth. These alternative processes will require additional steps to remove lignin as a waste stream that is typically burned. The present invention turns lignin into highly biodegradable intermediates at the treatment process. This also affords more rapid biological growth kinetics of fungi and with greater biomass conversion to fungi, relative to alternative treatment processes or traditional composting processes.

Additionally, the treatment produces a controllable amount of carbon dioxide and heat resulting in energy savings, while preserving a greater portion of cellulose and hemicellulose, which are unbound from lignin, resulting a more efficient process for producing fungus growth medium with more cellulose and hemicellulose preserved for the growth of fungi. Because of more cellulose and hemicellulose preservation, the treatment product has a higher energy content, in comparison with natural composting process that loses 3 to 4 times more cellulose and hemicellulose that are the primary food for mushrooms. It has been found that higher yields of fungi per mass of biomass feedstock may be achieved, not only improving revenues, but reducing biomass feedstock volumes, less storage space, less residual mushroom compost waste to be deposed, and reduced costs to achieve per unit mushroom output.

The treatment process of the invention accomplishes a similar oxidative breakdown of lignin in the lignocellulosic biomass caused by aerobic microorganisms in the composting process, but requiring from minutes to hours instead of weeks and months. In a typical composting process, aerobic microorganisms must degrade a portion of lignin before gaining access to the highly nutritive celluloses that will allow for a rapid growth phase. Extracellular oxidative enzymes, such as peroxidases and enzymes that produce chemical oxidants, such as hydrogen peroxide, oxalic acid, and veratryl alcohol are released by the microorganisms to cleave lignin into smaller, more oxygenated, soluble, hydrophilic metabolites, and concurrently make cellulose and hemicellulose accessible to the microorganisms for consumption. Since this enzymatic conversion occurs at the external surface, initial rates are limited by the characteristic porosity of the biomass. The composting process relying on microorganisms thus takes much longer and consumes a large portion of cellulose and hemicellulose in the biomass.

In some embodiments, the treatment process applies a pressure higher than atmospheric pressure, which may be performed in a reactor. Upon leaving the treatment reactor, the treated biomass may experience rapid depressurization to atmospheric pressure, which removes incondensable gases and some condensable vapors. It also induced a shearing force as these gases and vapors quickly leave the pores and spaces between fibers, resulting in further unbundling of cellulose and hemicellulose and making them more susceptible to biological metabolism when it is used for growing fungi. This pressure letdown is known as steam explosion. Through this process, the initial and ongoing accessibility to cellulose and hemicellulose by extracellular fungal hydrolytic enzymes is greatly increased as the porosity and external surface area are enhanced due to both significant removal of lignin and rapid steam explosion.

The treatment process significantly increases the accessibility of the cellulose and hemicellulose for downstream enzymatic treatments and/or fermentation processes. This will have a positive influence on downstream reaction kinetics and the degree of conversion of cellulose and hemicellulose to monomeric sugars. The overall yields in the downstream treatments are thus increased. In some embodiments, the yields achieved in the downstream treatments is close to the theoretical yield calculated based on the content of cellulose and hemicellulose in the biomass.

The fibers in the treated biomass have a fairly random orientation (FIG. 1). The fibers are fairly loose and not prone to compaction. These features are advantageous for successful growth of mushrooms and filamentous fungi, which require substrates to not have significant resistance to expansion for significant growth and deep penetration of filaments and mycelium in order to extract at high rates as much of the nutrients as possible from the treated biomass. In addition, the treated biomass has a structure sufficiently open (low density) containing void space throughout to allow adequate mass transfer of oxygen, carbon dioxide, water, extracellular hydrolytic enzymes, and nutrients to maximize and sustain growth of mushrooms and filamentous fungi.

In some embodiments, the treated biomass may be treated by a disc refiner to comminute the treated biomass even further.

Finally, it is also apparent that the higher temperatures and pressures used for the treatment process will result in a sterilized product to be used in the growth medium, without the presence of insects, microbial competitors or human pathogens. Thus, the long and energy costly pasteurization used in typical mushroom operations can be eliminated.

In summary, the growth medium of the invention includes the treatment product can be used for fungus production to not only accelerate the growth rate and the budding of fungi, but increases the extent of feedstock utilization, provides higher yields of fruiting bodies, lowers the demand of lignin degrading enzymes and oxidants which will add cost of mushroom production, and reduces the chance of infestation from competing microbes, pests and pathogens because it is sterilized.

The treated biomass is formulated into the growth medium for fungus by adjusting the moisture content to a level suitable for growth of fungus, and, if necessary, adjusting the pH of the treated biomass. In some embodiments, additional components may be added to (formulated into) the growth medium.

In some embodiments, the fungus growth medium further includes at least one additional component, selected from gypsum, inert materials, nitrogen supplement, carbon sources, proteinaceous sources, and minerals. Examples of inert materials include diatomaceous earth, sand, limestone chips, plastics or peat/sphagnum moss, fresh shredded feedstock and the like to limit growth medium compaction and permit higher rates of oxygen diffusion and mycelium growth and penetration.

In some embodiments, the growth medium includes a nitrogen supplement such as alfalfa press juice, monosodium glutamate, peptone, amino acids, urea, ammonium hydroxide, proteins, chicken manure, ammonium sulfate, ammonium phosphate, ammonium nitrate, calcium nitrate, and the like. Additional supplements include brewer's grain, seed meals of soybeans, peanuts, or cotton, and chicken manure, among others. The purpose of these nitrogen supplements is to increase the nitrogen content in the growth medium to a range of from about 1.0% to about 2.0%, or from about 1.5% to about 1.7% of the growth medium, both computed on a dry weight basis.

In some embodiments, the growth medium includes a source of soluble carbon for supporting fungus growth. Examples of soluble carbons include carbohydrates such as glucose, galactose, mannose, fructose, maltose, xylose, arabinose, dextrin, mannitol, sucrose, starch, sorbitol, lactose, rhamnose, etc., as well as natural sources of carbohydrates such as the hot water extract of straw, molasses, grain, potatoes, fruits, whey, etc., and their byproducts, fats and oils such as vegetable oils, animal fats, etc.

In some embodiments, the growth medium includes a proteinaceous source such as whey, blood meal, oil seed meals, alfalfa, brewer's byproducts, distiller's byproducts, and the like.

In some embodiments, the growth medium includes a mineral such as salts of calcium, phosphorus, sulphur, magnesium, potassium, iron, zinc, manganese, etc. The calcium may be selected from calcium sulfate, calcium carbonate, calcium bicarbonate, and ground gypsum.

In some embodiments, the growth medium includes an inoculation of synergistic mesophilic bacteria and bacterial communities that naturally assist in additional breakdown of the pretreated lignocellulosic material and may act as a protein and fine nutrient source for fungal growth. Examples of such organism include *Scytalidium thermophilum, Chaetomium thermophilum, Malbranchea sulfurea, Myriococcum thermophilum, Stilbella thermophila*, and *Thielavia terrestris*.

In some embodiments, the preprocessing may include additional steps of prewashing and/or preheating the biomass to remove undesirable contaminants from the biomass. In one example, prewashing may be carried out using an inclined wash table and several mass equivalents of hot demineralized water. The wash water, at a temperature of about 50 to 60° C. at the point of contact with the biomass, is distributed onto the biomass over a period of about 5 to 10 minutes.

This prewashing step offers multiple benefits for the treatment process. First, washing removes a significant portion, e.g. greater than 80 wt. % of the non-structural ash (dirt) carried within or on the biomass. Sand, rock, and dirt intermixed with the biomass accelerates the erosion and plugging of pipes, valves, and rotating equipment used in the treatment and downstream biological conversion steps. Cleaning the biomass ahead of treatment significantly reduces maintenance and operational costs in commercial operations, while increasing yields and overall facility efficiency.

Additionally, warm wash water successfully removes over 80% of the chloride resident within or on biomass such as harvested corn stover. It is highly beneficial to reduce the chloride level of biomass to concentrations under 200 ppmw. In doing so, cheaper stainless-steel alloys, like duplex stainless steel, can be used in the treatment reactor and other heated sections of the physical plant. At these lower levels of chloride, corrosion rates at the temperatures experienced in treatment are reduced to a level that does not require the use of more exotic expensive alloys.

Furthermore, the prewashing step encourages some amount of re-wetting, swelling, and pore and fiber bundle opening of field-dried or oven-dried biomass, like corn stover. Hydration increases accessibility to the bulk of the biomass and doing so enables greater rates of mass transfer of reactants, oxidizing agent, and solubilized intermediates in and out of the solid biomass during treatment. This may also shorten residence time in the reactor.

Moreover, the prewashing step permits the removal and recovery of water-soluble monomeric and oligomeric sugars and other soluble components present in the biomass, known collectively as extractives. For example, depending on the age and condition of corn stover, extractives can account for more than 20 wt. % of the dry weight and more than 44 wt. % of the total extractable mass can be carbohydrates.

These water extractives can represent a significant portion of the overall potential nutrients in the biomass. Since these simpler carbohydrates, carboxylic acids, and other components in the extractives tend to be more reactive than the more compact cellulose and hemicellulose fibers in the biomass, they are easily degraded from thermal and acid/base catalyzed reactions during the treatment process. Thus, they are typically lost during the treatment process and present a loss in potential fungus yields and/or growth rates. The invention collects and re-uses the water extractives for fungus growth would increase the yields and rates of fungi.

Another advantage of the invention is elimination of the odor from traditional composting process. One of the major hurdles facing mushroom growers is the strong foul-smelling atmospheric emissions from their composting operations, which limit their ability to locate or expand operations near major metropolitan areas. These close locations to large markets are economically attractive for growers given the short shelf life of harvested mushrooms, if not refrigerated, canned, or dries. Also, their low product density makes transportation costs high. The growth medium of the present invention avoids the odor issue by using a controlled treatment process of the biomass in a sealed reactor. This will permit mushroom growth near metropolitan or residential areas, reducing transportation and refrigeration costs, and ensuring fresher products being delivered to market. It also eliminates the need for surface water collection and treatment runoff water from manure and composting piles.

The fungi that can grow on the growth medium include macroscopic filamentous fungi (such as mushrooms), microscopic filamentous fungi, single celled microscopic yeasts, and multicellular filamentous molds. Some examples of fungi and their uses are listed as follows.
1) Non-Mushroom Fungi
  a) Yeasts
    i) *Sacchromyces cerevisiae*
      (1) Strains have been used as immunostimulants in previous research with fish (Gatesoupe, 2007; Oliva-Teles & Gonçalves, 2001).
      (2) Because its relatively high protein content, *S. cerevisiae* may be used as a protein source in commercial fish diets.
      (3) *Saccharomyces cerevisiae* contains between 40 and 65% protein with a similar amino acid profile to that of fishmeal (Nasseri et al., 2011).
    ii) *Wickerhamomyces anomalus*
      (1) Used in grain bio-preservation and as an anti-mold species due to its ability to outcompete molds and other yeasts (Tayel et al., 2013; Olstorpe & Passoth, 2011; Fredlund et al., 2004).
      (2) Ability to utilize various substrates for growth and by high phytase activity (Olstorpe et al., 2009; Vohra & Satyanarayana, 2001), making it a potential candidate for improving phosphorus absorption in fish.
      (3) Its reasonably high protein levels also make it a good candidate for use in animal feeds (Satyanarayana et al., 2012)
    iii) *Candida utilis*
      (1) Source of glucose
    iv) Consortium of fungi
      (1) Consortia of yeast gathered from wild fish species of interest (salt versus fresh versus tropic versus cold water) and supplement with yeast to help in the fermentation of treated biomass components (or maybe no supplementation needed). Fish food formulated with probiotics (living cultures).
      (2) The same can be true for poultry and livestock, in particular those animals that are reared open-range.
  b) Filamentous Fungi
    i) Ease in harvesting
    ii) Lower growth rates, lower protein content and acceptability than yeasts
    iii) Prefer a species that is not only edible, but naturally is inducible to colonize in pellets (granules)
      (1) Ease separation (if required)
      (2) Some mass transfer limitation, but could go to an aerated dilute bed reactor system
    iv) *Rhizopus oryzae*
      (1) Commonly grown on spent sulphite liquor, which is a waste product from paper pulp production (Ferreira et al., 2012; Edebo, 2008).
      (2) It possesses a similar amino acid profile to fish meal (Edebo, 2008; Mydland et al., 2007) and could be a good candidate for replacing fishmeal in the diet of fish (Ferreira et al., 2012; Edebo, 2008).
      (3) Contains polysaccharides, chitosan and chitin (glucosamine and N-acetylglucosamine polymers), integral parts of its cell wall, in variable amounts (Abro et al., 2014). These compounds, when fed to fish can have positive immunomodulatory effects (Harikrishnan et al., 2012; Esteban et al., 2001).
    v) *Neurospora intermedia*
      (1) Used for human consumption, for example in Indonesia.
    vi) *Aspergillus Niger, A. Oryzae*
      (1) Source of cellulose/hemicellulose
      (2) Making soy sauce (*A. Oryzae*)
    vii) *Cephalosporium eichhorniae*
      (1) Source of cellulose/hemicellulose
    viii) *Chaetomium celluloyticum*
      (1) Source of cellulose/hemicellulose
    ix) *Monascus purpureus*
      (1) Red rice yeast
      (2) Used in China to ferment a lot of foods x) *Fusarium venenatum*
   (1) Commercialized as SCP in Quorn
   (2) Sold in food supplements to vegetarians as an alternative to meat
   (3) On the market in UK since 1985
2) Multicellular Fungi (mushrooms)
   a) At the present time the only economical utilization of lignocellulosic wastes is in mushroom production.
   b) Spent mushroom growth medium is a valuable soil conditioner and a commodity product throughout the world
   c) Many mushrooms contain lignocellulolytic enzymes and are cultivated for food, lots of types used for human consumption mainly in Asia and Africa
   d) The industry appears ripe for a more scientific and engineering approach to understand elemental flows, ways to enhance growth rates, etc.
      i) *Agaricus bisporus*
         (1) An edible basidiomycete native to grasslands in Europe and North America
         (2) Portobello when mature
         (3) White button (common) when immature
      ii) *Volvariella* sp.
         (1) Cultured in rice straw in the Philippines and Southeast Asia.
         (2) Also favors wood chip piles.
         (3) Similar in appearance to death cap mushroom (Amanita phalloides)
      iii) *Lentinus edodes* sp.
         (1) Shiitake mushroom
         (2) Commercially, shiitake mushrooms are typically grown in conditions similar to their natural environment on either artificial substrate or hardwood logs, such as oak.
      iv) *Pleurotus* sp.
         (1) Oyster, abalone, or tree mushrooms
         (2) One of the most widely eaten mushroom families in the world
         (3) Pleurotus fungi have been used in mycoremediation of pollutants such as petroleum and polycyclic aromatic hydrocarbons
      v) *Auricularia polytricha*
         (1) Asian—China & Hawaii
         (2) Aka: Cloud ear fungus
      vi) *Enokitake*
         (1) A highly commercialized mushroom
         (2) Known for medicinal compounds and high protein stem
      vii) Medical mushrooms
         (1) Additional groups of mushrooms grown at small scale for the abstraction of key compounds used in health, traditional/non-traditional medicines
         (2) High value/low volume add on to the basic operation
            (a) *Agaricus subrufescens*
               (i) Anticancer activity
            (b) *Schizophyllum commune*
               (i) Anticancer activity
            (c) Many others Some examples of fungi include species from genera of *Agaricus*, *Lentinus* (Shiitake), *Morchella* (Morel), *Pleurotus* (oyster mushroom), *Flammulina* and *Volvariella*. Examples of fungal species include *Agaricus bisporus*, *Agaricus bitorquis*, *Agaricus brunnescens*, *Lentinus edodes*, *Morchella* sp., *Pleurotus* sp., *Flammulina velunpes*, *Volvariella volvacea*, *Lepisla nuda*, *Calocybe gambosa*, *Macrolepiola procera*, *Calvalia giganlean*, *Auricularia* spp., *Boletus* spp., *Lenlinula edodes*, *Canlharellus* spp., *Morchella* spp., *Pholiola nameko*, *Pleurolus* spp., *Slropharia rugosaannluala*, *Tremeila fuciformis*, *Volvariella volvacea*, *Grifola frondosa*, *Ganoderma* sp., *Polporus umbellalus*, *Hericium erinaceus*, *Coprinus comalus*, and *Agrocybe* sp.

Depending on the species of fungi, the fungal product may directed be consumed by the human population (such as mushrooms) or be fed to poultry, fish, livestock, and other animals, where eventually these animals are harvested as food for human populations. The latter route to human consumption is generally the case when growing single cell organisms that have a high nucleic acid content, which may induce gout in humans when the nucleic acid is consumed in high quantities.

Finally, the growth medium of the invention has residual solids after growth of fungi which include highly bioavailable fibers that enhance gut microflora of fish or livestock and provide readily available minerals, etc. Thus, in some embodiments, the residual solids after growth of fungi may be made into pellets for fish or livestock.

EXAMPLES

The following examples are illustrative, but not limiting, of the methods of the present disclosure. Other suitable modifications and adaptations of the variety of conditions and parameters normally encountered in the field, and which are obvious to those skilled in the art, are within the scope of the disclosure.

Example 1. Treatment of Corn Stover

In this example, corn stover (milled to small particles) was oxidized with oxygen as the oxidizing agent in accordance with the treatment process of the present invention. Corn stover was obtained from the U.S. Idaho National Laboratory Bioenergy Feedstock Library in bulk. The corn stover was a mixture of leaves, stalks, husks, and cobs. It was milled/shredded to particles with a size in the range of from a maximum length of 5 inches to a minimum length of 0.25 inch using a hammer mill.

The average composition of the corn stover was assayed using wet-chemical analysis methods developed and published by the US National Renewable Energy Laboratory. The composition of the corn stover, on a dry basis, is listed in the Table 1. The total ash content of the corn stover was about 7.54 wt. %, suggesting that there was some amount of dirt adhering to or distributed on the corn stover.

TABLE 1

Corn Stover Characterization

| Component | Wt. % |
| --- | --- |
| Cellulose | 40.3 |
| Hemicellulose | 23.7 |
| Other Polysaccharides | 4.4 |
| Lignin | 18.4 |
| Ash | 6.9 |
| Others | 6.3 |

The size-reduced corn stover was subjected to a prewashing step using several mass equivalents of hot demineralized water on an inclined wash table. The wash water had a temperature of about 50 to 60° C. at the point of contact with the corn stover and was evenly distributed onto the corn stover over a period of about 5 to 10 minutes. The wash water drained from the corn stover was collected, cleaned, and retained for later use in growing fungi.

The collected wash water contained extractives. The materials in the collected water included over 44 wt. % of simple carbohydrates (monomeric and polymeric sugars). Extractives in the example, on a dry basis, are given in Table 2.

TABLE 2

Corn Stover Extractives Composition

| Component | Wt. % |
| --- | --- |
| Proteins | 10.9% |
| Lignin | 12.0% |
| Polymeric Sugars | 12.4% |
| Glucan | 37.2% |
| Xylan | 22.3% |
| Galactan | 25.0% |
| Arabinan | 15.5% |
| Monomeric Sugars | 32.3% |
| Fructose | 45.4% |
| Glucose | 52.2% |
| Xylose | 2.3% |
| Ash | 15.5% |
| Organic Acids | 13.9% |
| Glycerol | 3.0% |

The collected wash water was neutralized with ammonium hydroxide, as necessary, and used in the growth of edible mushrooms.

The prewashed corn stover was then subjected to a pH-controlled oxidative treatment using a continuous rotating reactor designed for depolymerizing solid wet biomass at high temperature and pressure. Reaction temperature was held constant at 165° C. using a controlled amount of high temperature steam injected into the reactor. Reactor pressure was held constant at approximately 1379 kPa. Corn stover was metered to the reactor at a dry basis rate of about 19 kg per hour. Compressed air was also metered into the reactor at a mass rate of oxygen of about 14 wt. % of the dry biomass. The residence time for the corn stover in the reactor was held at 15 minutes.

Prior to entering the reactor, ammonium hydroxide was added to the wet corn stover to neutralize residual acidic components left after washing. During the course of the reaction, additional ammonium hydroxide was added to the reactor to maintain the pH of the treated biomass at about 5. The added amount of ammonium hydroxide was approximately 5 wt. % based on the weight of the dry corn stover.

Upon leaving the treatment reactor, the treated corn stover experienced rapid depressurization to atmospheric pressure, which removed incondensable gases and some condensable vapors. It also induced a shearing force as these gases and vapors quickly left the pores and spaces between fibers, resulting in further unbundling of cellulose and hemicellulose and making them more susceptible to biological metabolism when growing fungi.

Treated corn stover leaving the reactor had a composition as shown in Table 3. Very little cellulose was lost during the treatment process and less than 15 wt. % of potential xylose from hemicellulose was transformed to non-sugar products during the treatment process. As can be seen, much of the lignin was transformed to smaller compounds and functionalized to mostly carboxylic acids. Heat and carbon dioxide were also produced in the oxidative chain scission of lignin. Just as important was that essentially all lignin was altered in its chemical structure to convert the lignin from hydrophobic to hydrophilic.

Besides the products already noted, lignin decomposed into soluble components having molecular weights in excess of 300 g/mol (fulvic acids) and to insoluble components with molecular weights greater than 1000 g/mol (humic acids). Both of these materials are rapidly biodegraded by fungi for growth.

TABLE 3

Treated Corn Stover Composition

| Component | wt. % |
| --- | --- |
| Cellulose | 35.7% |
| C6 Sugar monomers | 0.6% |
| C6 Sugar oligomers | 0.6% |
| Hemicellulose | 12.1% |
| Xylose | 1.3% |
| Xylans | 9.0% |
| Other Polysaccharides | 3.8% |
| Volatile Fatty Acids | 6.0% |
| Fulvic Acids | 1.7% |
| Humic Acids | 4.6% |
| Others | 3.7% |
| Ash | 5.3% |

The treated corn stover had a texture, color, and pliability quite similar to that of natural composted straw or hay, which is typically used to grow mushrooms such as *Agaricus bisporus*. The fiber orientation in the treated corn stover was fairly random, individual, and non-binding. The fibers were fairly loose and not prone to compaction (FIG. 1), which allows significant growth and deep penetration of filaments and mycelium in order to extract at high rates as much of the nutrients from the treated corn stover as possible. Upon cooling, the treated corn stover was ready for growing fungi.

Example 2. Growth of *Agaricus bisporus* on Treated Corn Stover 45.4 Kg of dry corn stover treated by the method of the present invention is cooled to an ambient temperature and combined with gypsum, crushed limestone, lime, and nitrogen fertilizer, to obtain a growth medium containing about 2.3 wt. % nitrogen, approximately 4.0 wt. % gypsum, both on a dry weight basis, and a pH of about 7.5. The moisture content of the growth medium is adjusted to approximately 70 wt. % and then the growth medium was poured into trays. The growth medium in the trays is thoroughly mixed with *Agaricus bisporus* spawn in an amount of about 2.5 wt. % spawn on a dry weight basis. Sensors for moisture, temperature, and pH are used in each tray for monitoring the growth medium.

Trays with the growth medium are then relocated in a climate-controlled room kept at approximately 95% relative humidity. During the vegetative growth phase, the room temperature is adjusted to maintain tray bed temperatures of about 23.9+/−1° C. with little or no fresh air addition. The growth medium is watered as needed to maintain the moisture content of the growth medium. The spawn-run concludes at 12 days, at which point a casing layer of limestone-treated sphagnum peat moss is applied atop the growth medium. The case-run is conducted at similar environmental conditions as are used in the spawn-run and concluded in 7 days when mycelium has penetrated troughs of the casing layer.

At this point, the room temperature is reduced to 15.6° C., and fresh air is introduced to lower and maintain the carbon dioxide concentration in the room below 1000 ppm, and the relative humidity in the room is adjusted to 85%, in order to induce mushroom pinning and subsequent cropping. After pin formation, which takes approximately 7 days, both corn stover wash water and fresh water are used to water the casing layer.

Flush breaks are set at a maximum of 5 days, depending on the intensity of growth during the flush. At the end of each flush break period, all mushrooms are harvested from the trays. Three flush breaks are used to measure growth efficiency. Harvested mushrooms are expected to be normal white in appearance with no signs of discoloration, having well rounded caps with veils intact, having a good flavor, and being firm to the touch. The total amount of mushrooms harvested is predicted to be approximately 66.7 Kg in three successive flushes of 25.4 Kg, 22.2 Kg, and 19.1 Kg, respectively.

Comparative Example 2A. Growth of *Agaricus bisporus* on Composted Corn Stover 45.4 Kg of dry corn stover is wetted and combined with gypsum and nitrogen fertilizer and composted by the traditional composting method for a period of approximately 3 weeks, to obtain a growth substrate containing about 2.3 wt. % nitrogen and approximately 4.0 wt. % gypsum, both on a dry weight basis. The moisture content of the composted substrate is adjusted to approximately 68 wt. % and then the composted substrate was poured into trays. The growth substrate in trays is thoroughly mixed with *Agaricus bisporus* spawn in an amount of about 2.5 wt. % spawn on a dry weight basis. Sensors for moisture, temperature, and pH are used in each tray for monitoring the growth substrate.

Trays are relocated to a climate-controlled room kept at approximately 95% relative humidity. During the vegetative growth phase, the room temperature is adjusted to maintain tray bed temperatures of about 23.9+/−1° C. with little or no fresh air addition. The trays are watered as needed to maintain the moisture content in the substrate. The spawn-run concludes at 12 days, at which point a casing layer of limestone-treated sphagnum peat moss is applied atop the growth substrate. The case-run is conducted at similar environmental conditions as are used in the spawn-run and concluded in 7 days when mycelium has penetrated troughs of the casing layer.

At this point, the room temperature is reduced to 15.6° C., and fresh air is introduced to lower and maintain carbon dioxide concentrations below 1000 ppm. The relative humidity in the room is adjusted to 85% in order to induce mushroom pinning and subsequent cropping. After pin formation, which takes approximately 7 days, fresh water is used to water the casing layer.

Flush breaks are set at a maximum of 5 days, depending on the intensity of mushroom growth during the flush. At the end of each flush break period, all mushrooms are harvested from the trays. Three flush breaks are used to measure growth efficiency. Harvested mushrooms are expected to be normal white in appearance with no signs of discoloration, having well rounded caps with veils intact, having a good flavor, and being firm to the touch. The total amount of mushrooms harvested is predicted to be approximately 44.0 Kg in three successive flushes of 17.2 Kg, 16.3 Kg, and 10.4 Kg.

Example 3. Growth of *Agaricus bisporus* on Treated Wheat Straw 45.4 Kg of dry wheat straw treated by the method of the present invention is cooled to ambient temperature and combined with gypsum, crushed limestone, lime, and nitrogen fertilizer to obtain a growth medium containing about 2.3 wt. % nitrogen and approximately 4.0 wt. % gypsum, both on a dry basis, and having a pH of about 7.5. The moisture content of the growth medium is adjusted to approximately 71 wt. % and then the growth medium is poured into trays. The growth medium in the trays is thoroughly mixed with *Agaricus bisporus* spawn in an amount of about 2.5 wt. % spawn on a dry weight basis. Sensors for moisture, temperature, and pH are used in each tray for monitoring the growth medium.

Trays with the growth medium are then relocated in a climate-controlled room kept at approximately 95% relative humidity. During the vegetative growth phase, the room temperature is adjusted to maintain tray bed temperatures of about 23.9+/−1° C. with little or no fresh air addition. The growth medium is watered as needed to maintain the moisture content of the growth medium. The spawn-run concludes at 12 days. A casing layer of limestone-treated sphagnum peat moss is applied atop the growth medium. The case-run is conducted at similar environmental conditions as used in the spawn-run and concluded in 7 days when mycelium has penetrated troughs of the casing layer.

At this point, the room temperature was reduced to 15.6° C., and fresh air is introduced to lower and maintain the carbon dioxide concentration below 1000 ppm. The relative humidity is adjusted to 85% in order to induce mushroom pinning and subsequent cropping. After pin formation, which took approximately 7 days, both straw wash water and fresh water are used to water the casing layer.

Flush breaks are set at a maximum of 5 days, depending on the intensity of growth during the flush. At the end of each flush break period, all mushrooms are harvested from the trays. Three flush breaks are used to measure biological efficiency. Harvested mushrooms are expected to be normal white in appearance with no signs of discoloration, having well rounded caps with veils intact, having a good flavor, and being firm to the touch. The total amount of mushrooms harvested is predicted to be approximately 71.7 Kg in three successive flushes of 25.9 Kg, 25.5 Kg, and 21.3 Kg, respectively.

Comparative Example 3A. Growth of *Agaricus bisporus* on Composted Wheat Straw 45.4 Kg of wheat straw is wetted and combined with gypsum and nitrogen fertilizer and composted by the traditional two-step method for a period of approximately 3 weeks, to obtain a growth substrate containing about 2.3 wt. % nitrogen, approximately 4.0 wt. % gypsum, both on a dry weight basis. The moisture content of the growth substrate is adjusted to approximately 67 wt. % and then the growth substrate is poured into trays. The growth substrate in the trays is thoroughly mixed with *Agaricus bisporus* spawn in an amount of about 2.5 wt. % spawn on a dry weight basis. Sensors for moisture, temperature, and pH are inserted into each tray for monitoring the growth substrate.

Trays with the growth substrate are relocated in a climate-controlled room kept at approximately 95% relative humidity. During the vegetative growth phase, the room temperature is adjusted to maintain tray bed temperatures of about 23.9+/−1° C. with little or no fresh air addition. The growth substrate is watered as needed to maintain the moisture content of the growth substrate. The spawn-run concludes at 12 days, at which point a casing layer of limestone-treated sphagnum peat moss is applied on top of the growth substrate. The case-run is conducted at similar environmental conditions as used in the spawn-run and concludes in 7 days when mycelium has penetrated troughs of the casing layer.

At this point, the room temperature is reduced to 15.6° C., and fresh air is introduced to lower and maintain the carbon dioxide concentration below 1000 ppm. The relative humidity is adjusted to 85% in order to induce mushroom pinning and subsequent cropping. After pin formation, which takes approximately 7 days, fresh water is used to water the casing layer.

Flush breaks are set at a maximum of 5 days, depending on the intensity of growth during the flush. At the end of each flush break period, all mushrooms are harvested from the trays. Three flush breaks are used to measure growth efficiency. Harvested mushrooms are expected to be normal white in appearance with no signs of discoloration, having well rounded caps with veils intact, having a good flavor, and being firm to the touch. The total amount of mushrooms harvested is predicted to be approximately 45 Kg in three successive flushes of 17.7 Kg, 16.8 Kg, and 10.4 Kg.

Example 4. Growth of *Agaricus bisporus* on Treated Poplar Wood Chips 45.4 Kg of poplar wood chips treated by the method of the present invention is cooled to ambient temperature and combined with gypsum, crushed limestone, lime, and nitrogen fertilizer, to obtain a growth medium containing about 2.3 wt. % nitrogen and approximately 4.0 wt. % gypsum, both on a dry weight basis, and having a pH of about 7.5. The moisture content of the growth medium is adjusted to approximately 71 wt. % and then the growth medium is poured into trays. The growth medium in the trays is thoroughly mixed with *Agaricus bisporus* spawn in an amount of about 2.5 wt. % spawn on a dry weight basis. Sensors for moisture, temperature, and pH are inserted into each tray for monitoring the growth medium.

Trays with the growth medium are relocated in a climate-controlled room kept at approximately 95% relative humidity. During the vegetative growth phase, the room temperature is adjusted to maintain tray bed temperatures of about 23.9+/−1° C. with little or no fresh air addition. The growth medium is watered as needed to maintain the moisture content of the growth medium. The spawn-run concludes at 12 days, at which point a casing layer of limestone-treated sphagnum peat moss is applied atop the growth medium. The case-run is conducted at similar environmental conditions as used in the spawn-run and concluded in 7 days when mycelium has penetrated troughs of the casing layer.

At this point, the room temperature is reduced to 15.6° C., and fresh air is introduced to lower and maintain the carbon dioxide concentration below 1000 ppm. The relative humidity in the room is adjusted to 85% in order to induce mushroom pinning and subsequent cropping. After pin formation, which takes approximately 7 days, both wood chip wash water and fresh water are used to water the casing layer.

Flush breaks are set at a maximum of 5 days, depending on the intensity of growth during the flush. At the end of each flush break period, all mushrooms are harvested from the trays. Three flush breaks are used to measure growth efficiency. Harvested mushrooms are expected to be normal white in appearance with no signs of discoloration, having well rounded caps with veils intact, having a good flavor, and being firm to the touch. The total amount of mushrooms harvested is predicted to be approximately 75.3 Kg in three successive flushes of 27.2 Kg, 25.9 Kg, and 22.2 Kg.

Comparative Example 4A. Growth of *Agaricus bisporus* on Composted Poplar Shavings 45.4 Kg of poplar shavings are wetted and combined with gypsum and nitrogen fertilizer and composted by the traditional two-step method for a period of approximately 3 weeks, to obtain a growth substrate containing about 2.3 wt. % nitrogen and approximately 4.0 wt. % gypsum, both on a dry weight basis. The moisture content of the growth substrate is adjusted to approximately 67 wt. % and then the growth substrate is poured into trays. The growth substrate in the trays is thoroughly mixed with *Agaricus bisporus* spawn at a rate of about 2.5 wt. % spawn on a dry substrate basis. Sensors for moisture, temperature, and pH are inserted into each tray for monitoring the growth substrate.

Trays with the growth substrate are relocated in a climate-controlled room kept at approximately 95% relative humidity. During the vegetative growth phase, the room temperature is adjusted to maintain tray bed temperatures of about 23.9+/−1° C. with little or no fresh air addition. The growth substrate is watered as needed. The spawn-run concludes at 12 days, at which point a casing layer of limestone-treated sphagnum peat moss is applied atop the growth substrate. The case-run is conducted at similar environmental conditions as used in the spawn-run and concludes in 7 days when mycelium has penetrated troughs of the casing layer.

At this point, the room temperature is reduced to 15.6° C., and fresh air is introduced to lower and maintain the carbon dioxide concentration below 1000 ppm. The relative humidity in the room is adjusted to 85% in order to induce mushroom pinning and subsequent cropping. After pin formation, which takes approximately 7 days, fresh water is used to water the casing layer.

Flush breaks are set at a maximum of 5 days, depending on the intensity of growth during the flush. At the end of each flush break period, all mushrooms are harvested from the trays. Three flush breaks are used to measure growth efficiency. Harvested mushrooms are expected to be normal white in appearance with no signs of discoloration, having well rounded caps with veils intact, having a good flavor, and being firm to the touch. The total amount of mushrooms harvested is predicted to be approximately 29.5 Kg in three successive flushes of 11.3 Kg, 10.9 Kg, and 7.7 Kg.

Example 5. Growth of *Lentinula edodes* on Treated Poplar Wood Chips 45.4 Kg of poplar wood chips treated by the method of the present invention is cooled to ambient temperature and combined with gypsum, crushed limestone, and wheat bran, to obtain a growth medium containing about 10 wt. % bran and approximately 2.5 wt. % gypsum, both on a dry basis, and having a pH of about 5.7. The moisture content of the growth medium is adjusted to approximately 60 wt. % and then the growth medium is poured into bags with filtered breathing windows. The growth medium in the bags is placed in a climate-controlled room and inoculated with *Lentinula edodes* spawn in an amount of about 2.5 wt. % spawn on a dry weight basis. The growth medium in bags, referred to as synthetic logs, is kept at approximately 60% relative humidity.

During the mycelium growth phase, the room temperature is adjusted to maintain growth medium temperatures of about 23.9+/−1° C. with no fresh air addition and little or no light. At the 25-day point, the bags are removed from the synthetic logs to induce initiation of primordia growth by water soaking the synthetic logs, thermal shocking at 12.2° C. for 4 hours, then raising the temperature to 17.8° C., adjusting relative humidity to 95%, applying fresh air to keep the carbon dioxide concentration below 1000 ppm, and applying periods of light.

After 6 days, fruiting is induced by cycling the temperature from 17.8° C. to 23.9° C. and reducing relative humidity to 65%. After harvesting fruits are complete, the logs are put into dormancy by lowering relative humidity to about 40% at 21.1° C. for 9 days, after which the logs are soaked for 10 hours for the next flush and harvest. Three flushes are conducted and the total mushroom yield is predicted to be 66.7 Kg.

Comparative Example 5A. Growth of *Lentinula edodes* on Poplar Wood Shavings 45.4 Kg of poplar wood shavings and coarse sawdust are combined with gypsum and wheat bran to obtain a growth substrate containing about 10 wt. % bran, and approximately 2.5 wt. % gypsum, both on a dry weight basis. The growth substrate is pasteurized at 60° C. for 4 hours using steam and air. Upon cooling, the moisture content of the growth substrate is adjusted to approximately 60 wt. % and then poured into bags with filtered breathing windows, placed in a climate-controlled room and inoculated with *Lentinula edodes* spawn in an amount of about 2.5 wt. % spawn on a dry weight basis.

The growth substrate in bags, referred to as synthetic logs, is kept at approximately 60% relative humidity. During the mycelium growth phase, the room temperature is adjusted to maintain log temperatures of about 23.9+/−1° C. with no fresh air addition and little or no light. At the 25-day point, the bags are removed from the synthetic logs. The primordia growth is initiated by water soaking the logs, thermal shocking at 12.2° C. for 4 hours, then raising the temperature to 17.8° C., adjusting relative humidity to 95%, applying active fresh air addition to keep the carbon dioxide concentration below 1000 ppm, and applying periods of light.

After 6 days, fruiting was induced by cycling the temperature from 17.8° C. to 23.9° C. and reducing relative humidity to 65%. After harvesting fruits is complete, the logs are put into dormancy by lowering relative humidity to about 40% at 21.1° C. for 9 days, after which the logs are soaked for 10 hours for the next flush and harvest. Three flushes are conducted and the total mushroom yield is predicted to be 30.9 Kg.

Using the growth media of the invention, the time period for the *Agaricus bisporus* to grow to the first harvest can be reduced by 2 to 3 days, relative to using a traditional compost from the same biomass. Yields for both systems on the first harvest are expected to be similar, because of mushroom crowding. However, the yields of second and third harvests are expected to be not only faster, but greater in mass for the growth media of the invention, relative to the traditional compost, due to the higher available carbohydrate content and the greater surface exposure from the transformation of lignin in the growth media. Also, upon budding and fruiting of mushrooms, watering the mushroom beds using the wash water of biomass (e.g., corn stover) containing additional carbohydrates, soluble minerals, proteins can provide additional nutrients for the mushrooms.

The growth of mushrooms is measured by biological efficiency, which is the amount of fresh mushrooms over unit amount of dry biomass feedstock. The net result of the treatment is an increase in biological efficiency from 1 to 1.5 for traditional compost to 2.58 for treated biomass. This means that each pound of dry biomass feedstock, after treatment of the invention, can product a total of 2.58 pounds of fresh mushrooms. On the other hand, each pound of dry biomass feedstock, after the traditional composting process, can produce a total of from 1 to 1.5 pounds of fresh mushrooms.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meanings of the terms in which the appended claims are expressed.

All documents mentioned herein are hereby incorporated by reference in their entirety or alternatively to provide the disclosure for which they were specifically relied upon. The applicant(s) do not intend to dedicate any disclosed embodiments to the public, and to the extent any disclosed modifications or alterations may not literally fall within the scope of the claims, they are considered to be part hereof under the doctrine of equivalents.

What is claimed is:

1. A method for producing a growth medium for fungus from a lignocellulosic biomass, comprising steps of:
   (a) directly treating a mixture of the lignocellulosic biomass and water with at least one oxidizing agent and steam at a temperature in a range of from about 130° C. to about 220° C. for a period from about 5 seconds to about 10 hours to produce a treated biomass;
   (b) periodically measuring a pH of the mixture for substantially an entire duration of step (a);
   (c) as necessary, based on the pH of the mixture measured in step (b), adjusting the pH of the mixture into a range of from about pH 4.5 to about pH 7.5 by adding a base to the mixture;
   (d) adjusting a water content of the treated biomass into a range of 60-80 wt. % to provide the growth medium; and
   (e) adding an inert material to the treated biomass, wherein the inert material is selected from the group consisting of diatomaceous earth, sand, limestone chips, plastics and peat moss.

2. The method of claim 1, further comprising a step of adding a nitrogen supplement selected from the group consisting of alfalfa press juice, monosodium glutamate, peptone, amino acids, urea, ammonium hydroxide, proteins, chicken manure, ammonium sulfate, ammonium phosphate, ammonium nitrate, calcium nitrate, brewer's grain, seed meal of soybeans, seed meal of peanuts, seed meal of cotton, and chicken manure.

3. The method of claim 2, wherein the nitrogen supplement is added to reach a nitrogen content in the growth medium to a range of from about 1.0% to about 2.0% of the growth medium, on a dry weight basis.

4. The method of claim 1, further comprising a step of adding a mineral selected from the group consisting of salts of calcium, phosphorus, sulphur, magnesium, potassium, iron, zinc, and manganese.

5. The method of claim 4, wherein the mineral is a salt of calcium selected from the group consisting of calcium sulfate, calcium carbonate, calcium bicarbonate, and ground gypsum.

6. The method of claim 1, further comprising a step of adding a bacterium to the growth medium for breaking down the treated biomass.

7. The method of claim 6, wherein the bacterium is selected from the group consisting of *Scytalidium thermophilum*, *Chaetomium thermophilum*, *Malbranchea sulfurea*, *Myriococcum thermophilum*, *Stilbella thermophila*, and *Thielavia terrestris*.

8. The method of claim 1, wherein the biomass is selected from the group consisting of corn stover, corn cobs, palm tree empty fruit bunches, sugar cane bagasse, straw from grain crops, hay, wood waste from thinnings of deciduous and conifer forestry, sawdust from lumbering and furniture making, guayule residuals after natural rubber extraction, waste paper and cardboard.

9. The method of claim 1, wherein the at least one oxidizing agent is selected from the group consisting of air, oxygen enriched air, oxygen, ozone, perchlorates, carbon dioxide, nitrous oxide, oxides, superoxides, permanganates, chlorates, peroxides, hypochlorites, and nitrates.

10. The method of claim 1, wherein the range for the pH of the mixture is from about pH 6.0 to about pH 7.0.

11. The method of claim 1, wherein the base is selected from the group consisting of oxides, hydroxides, carbonates, borates, and halogenates of Group I and Group II elements.

12. The method of claim 1, wherein the base is selected from the group consisting of ammonia, ammonium hydroxide, urea and combinations thereof.

13. The method of claim 1, wherein the temperature is in a range of from about 150° C. to about 180° C.

14. The method of claim 1, wherein step (a) is performed under a pressure in a range of from about 308.2 KPa to about 928.7 KPa.

15. The method of claim 1, wherein the period of the treating step is from about 1 minute to about 7 hours.

16. The method of claim 1, wherein the mixture further comprises an oxidation catalyst selected from the group consisting of water insoluble metals, transition metals, precious metals, their salts or oxides, and combinations thereof.

17. The method of claim 1, further comprising a step of adding a source of soluble carbon selected from the group consisting of glucose, galactose, mannose, fructose, maltose, xylose, arabinose, dextrin, mannitol, sucrose, starch, sorbitol, lactose and rhamnose.

18. The method of claim 1, further comprising a step of adding a carbon source selected from the group consisting of molasses, grain, potatoes, fruits, whey, and their byproducts.

19. The method of claim 1, further comprising a step of adding a proteinaceous source to the treated biomass, wherein the proteinaceous source is selected from the group consisting of whey, blood meal, oil seed meals, alfalfa, brewer's byproducts, and distiller's byproducts.

* * * * *